US008835473B2

(12) United States Patent
Goydos et al.

(10) Patent No.: US 8,835,473 B2
(45) Date of Patent: Sep. 16, 2014

(54) METHODS AND COMPOSITIONS FOR TREATING CANCER

(75) Inventors: James S. Goydos, East Brunswick, NJ (US); Suzie Chen, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 198 days.

(21) Appl. No.: 12/560,119

(22) Filed: Sep. 15, 2009

(65) Prior Publication Data

US 2010/0221246 A1 Sep. 2, 2010

Related U.S. Application Data

(63) Continuation-in-part of application No. 11/855,890, filed on Sep. 14, 2007, now Pat. No. 7,691,377, which is a continuation-in-part of application No. 11/091,076, filed on Mar. 28, 2005, now Pat. No. 7,385,103.

(60) Provisional application No. 61/097,029, filed on Sep. 15, 2008, provisional application No. 60/649,022, filed on Feb. 1, 2005, provisional application No. 60/563,131, filed on Apr. 16, 2004.

(51) Int. Cl.
*A61K 31/425* (2006.01)

(52) U.S. Cl.
USPC ............................................. 514/367

(58) Field of Classification Search
CPC ... C07D 417/12; C07D 277/82; A61K 31/428
USPC ....................................... 514/367
See application file for complete search history.

(56) References Cited

U.S. PATENT DOCUMENTS

| | | | |
|---|---|---|---|
| 5,869,609 A | 2/1999 | Mulvihill et al. | |
| 6,589,991 B1 | 7/2003 | Lai et al. | |
| 6,589,998 B1 * | 7/2003 | Ron et al. | 514/772.4 |
| 6,797,692 B1 * | 9/2004 | Ikonomidou | 424/85.2 |
| 6,923,966 B2 | 8/2005 | Rybak et al. | |
| 6,998,391 B2 * | 2/2006 | Lyons et al. | 514/49 |
| 7,129,073 B2 | 10/2006 | Liu et al. | |
| 7,456,267 B2 | 11/2008 | Elson et al. | |
| 7,691,377 B2 * | 4/2010 | Goydos et al. | 424/138.1 |
| 2005/0235366 A1 | 10/2005 | Chen | |

OTHER PUBLICATIONS

Matz. Riluzole. CNS Drug Reviews, vol. 2, No. 1, pp. 40-51.*
Rzeski et al. Glutamate antagonists limit tumor growth. PNAS, vol. 98, No. 11, May 22, 2001, 6372-6377.*
National Cancer Institute. Definition of antagonist. Electronic Resource. [http://www.cancer.gov/dictionary/?print=1&cdrid=350250. Retrieved on Oct. 28, 2012.*
Matz. Riluzole. CNS Drug Reviews, vol. 2, No. 1. pp. 40-51. 1996.*
Ahmad et al., "BAY 43/9006 in patients with advanced melanoma: The Royal Marsden experience," Proc Am Soc Clin Oncol 22(14S): 7115, abstract No. 7506, Jul. 15 Supplement, 2004.
Aiba et al., "Reduced hippocampal long-term potentiation and context-specific deficit in associative learning in mGluR1 mutant mice," Cell 79(2): 365-375, Oct. 21, 1994.
Aiba et al., "Deficit cerebellar long-term depression and impaired motor learning in mGluR1 mutant mice," Cell 79(2): 377-388, Oct. 21, 1994.
Carson et al., "A phase 2 trial of a recombinant humanized monoclonal anti-vascular endothelial growth factor (VEGF) antibody in patients with malignant melanoma," Proc Am Soc Clin Oncol 22:715, abstract No. 2873, 2003.
Chen et al., "Spontaneous Melanocytosis in Transgenic Mice," J Invest Dermatol 106: 1145-1151, 1996.
Chen et al., "Aberrant expression of metabotropic glutamate receptor 1 (GRM1) in human melanoma," Melanoma X and The Third Annual International Melanoma Research Congress, Sep. 14-16, 2006; pp. 158-161.
Cohen-Solal et al., "Development of Cutaneous Amelanotic Melanoma in the Absence of a Functional Tyrosinase," Pigment Cell Res 14: 466-474, 2001.
Colón-Teicher et al., "Genomic sequences capable of committing mouse and rat fibroblasts to adipogenesis," Nucleic Acids Research 21(9): 2223-2228, 1993.
Conquet et al., "Motor deficit and impairment of synaptic plasticity in mice lacking mGluR1," Nature 372(6503): 237-243, Nov. 17, 1994.
Marin et al., "Grm5 expression is not required for the oncogenic role of Grm1 in melanocytes," Neuropharmacology 49(Supp 1): 70-79, 2005.
Millward et al., "Randomized multinational phase 3 trial of dacarbazine (DTIC) with or without Bcl-2 antisense (oblimersen sodium) in patients (pts) with advanced malignant melanoma (MM): Analysis of long-term survival," Proc Am Soc Olin Oncol 22(14S): 7505, Jul. 15 Supplement, 2004.
Namkoong et al., "Metabotropic Glutamate Receptor 1 and Glutamate Signaling in Human Melanoma," Cancer Res 67(5): 2298-2305, Mar. 1, 2007.
Pollock et al., "Melanoma mouse model implicates metabotropic glutamate signaling in melanocytic neoplasia," Nature Genetics 34: May 1-5, 2003.
Skerry et al., "Glutamate Signalling in Non-Neuronal Tissues," Trends in Pharmacological Sciences 22(4): 174-181, 2001.
Stepulak et al., "NMDA antagonist inhibits the extracellular signal-regulated kinase pathway and suppresses cancer growth," Proc Nat'l Acad Sci 102(43): 15605-15610, Oct. 25, 2005.
Zhu et al., "Development of Heritable Melanoma in Transgenic Mice," J Invest Dermatol 110: 247-252, 1998.
Haas et al: "The non-competitive metabotropic glutamate receptor-1 antagonist CPCCOEt inhibits the in vitro growth of human melanoma",Oncology Reports, vol. 17, No. 6, Jun. 2007, pp. 1399-1404.

(Continued)

*Primary Examiner* — Anna Pagonakis
(74) *Attorney, Agent, or Firm* — Fox Rothschild LLP

(57) ABSTRACT

The present invention provides methods of treating cancer using 2-amino-6-trifluoromethoxybenzothiazole (riluzole). In one aspect, the present invention provides methods of reducing cancer cell growth. In another aspect, the present invention provides a method of inducing apoptosis in a cancer cell. In another aspect, the present invention provides a method of reducing the growth of a glutamate-releasing tumor.

22 Claims, 5 Drawing Sheets

(56) References Cited

OTHER PUBLICATIONS

Atallah et al: "Treatment of metastatic malignant melanoma.",Current Treatment Options in Oncology, May 2005, vol. 6, No. 3, May 2005, pp. 185-193.

Eisen T et al: "Sorafenib in advanced melanoma: a Phase II randomised discontinuation trial analysis",British Journal of Cancer, vol. 95, No. 5, Sep. 2006, pp. 581-586.

* cited by examiner

METHODS AND COMPOSITIONS FOR TREATING CANCER

CROSS-REFERENCE TO RELATED APPLICATION

This application claims the benefit under 35 U.S.C. §119(e) of U.S. Provisional Patent Application No. 61/097,029, filed Sep. 15, 2008; and is a continuation-in-part of U.S. patent application Ser. No. 11/855,890, filed Sep. 14, 2007 (now pending); which is a continuation-in-part of U.S. patent application Ser. No. 11/091,076, filed Mar. 28, 2005 (U.S. Pat. No. 7,385,103); which claims the benefit under 35 U.S.C. §119(e) of U.S. Provisional Patent Application No. 60/649,022, filed Feb. 1, 2005, and U.S. Provisional Patent Application No. 60/563,131, filed Apr. 16, 2004. The disclosures of each of the foregoing applications are incorporated herein by reference in their entirety.

STATEMENT OF GOVERNMENT INTEREST

The U.S. Government has a paid-up license in this invention and the right in limited circumstances to require the patent owner to license others on reasonable terms as provided for by the terms of Grant No. RO1CA108720 awarded by the National Institutes of Health and Grant No. ES05022 awarded by the National Institute of Environmental Health Sciences.

BACKGROUND

1. Technical Field

The invention generally relates to methods of treating cancer. Particularly, the invention relates to methods of reducing cancer cell growth, proliferation, and/or metastasis using 2-amino-6-trifluoromethoxybenzothiazole (riluzole).

2. Description of the Related Art

The incidence of melanoma has been increasing for the past several years. In the United States, more than 60,000 patients are estimated to be diagnosed with melanoma with approximately 8,000 deaths in 2006. The overall lifetime risk of developing melanoma is 1 in 77 for women and 1 in 52 for men.

Melanomas vary greatly in aggressiveness. Very aggressive melanomas grow rapidly, metastasize early, and progress quickly, while less aggressive melanomas grow with a more indolent course. Consequently, much effort has gone into defining the characteristics of the more aggressive melanoma phenotype in hopes of designing therapies that target these more aggressive tumors and sparing patients with less aggressive melanomas often toxic adjuvant therapy designed to lessen the likelihood of recurrence and metastasis.

Metastasis is a multistep process requiring a melanoma cell to escape the control of the local microenvironment and invade the basement membrane. Once in contact with the interstitial microenvironment, integrins on the melanoma cell surface bind to the extracellular matrix (ECM) and this initiates signal transduction events that promote cell survival, migration, and invasion. One signal transduction pathway that appears to be important in melanoma progression is the mitogen activated protein kinase (MAPK) pathway. This signaling pathway begins with Ras activation and proceeds through the activation of Raf and MEK 1/2, resulting in the activation of ERK 1/2. The MAPK pathway controls processes central to melanoma progression, including cell growth, apoptosis, and cell migration. For instance, activation of this pathway leads to upregulation of the expression of proteases such as urokinase-type plasminogen activator (uPA), matrix metalloproteinases (MMP), and tissue plasminogen activator (tPA) that break down the surrounding collagen matrix and promote cell invasion and migration.

Phenotypically aggressive melanoma cells are also very plastic, able to mimic the activities of endothelial cells and to participate in processes such as neovascularization and the formation of fluid-conducting, matrix-rich meshworks. This vasculogenic mimicry has been shown to be a common characteristic of aggressive melanomas and appears to be controlled by complex signal transduction networks within the cell. Indeed, one of the main signaling cascades involved in vasculogenic mimicry is the MAPK pathway, and blocking the phosphorylation of ERK1/2 results in an inhibition of vasculogenic mimicry in three dimensional collagen cultures.

With increased knowledge of the genetic alterations that lead to a more aggressive melanoma phenotype, investigators have been searching for strategies designed to interrupt the relevant signaling pathways and result in either the inhibition of melanoma progression or the preferential killing of melanoma cells. However, different genetic alterations can lead to the activation of the same cellular pathways and inhibiting one pathway component, such as Raf, may not be an effective strategy if other genetic alterations result in downstream target activation. Consequently, we need to continue to work out the relevant signal transduction networks to be able to develop therapies to treat patients with melanoma.

BRIEF SUMMARY

In various embodiments, the present invention contemplates, in part, a method for reducing cancer cell growth comprising contacting a cancer cell with an amount of 2-amino-6-trifluoromethoxybenzothiazole (riluzole), thereby reducing cancer cell growth. In one embodiment, the cancer cell expresses GRM1 and/or is a glutamate-releasing cancer cell.

In various other embodiments, the present invention contemplates, in part, a method to induce apoptosis in a cancer cell by contacting the cancer cell with an amount of riluzole, thereby inducing apoptosis in the cancer cell. In one embodiment, the cancer cell expresses GRM1 and/or is a glutamate-releasing cancer cell.

In a particular embodiment, the cancer cell is a glutamate-releasing cancer cell selected from the group consisting of: a melanoma cell, a colon adenocarcinoma cell, a breast carcinoma cell, a thyroid carcinoma cell, a lung carcinoma cell, a glioma cell, a neuroblastoma cell, and a lymphoma cell.

In a particular embodiment, the cancer cell is selected from the group consisting of: a colon adenocarcinoma cell, a breast carcinoma cell, a thyroid carcinoma cell, a lung carcinoma cell, a glioma cell, a neuroblastoma cell, and a lymphoma cell.

In one embodiment, the cancer cell is a GRM1 expressing cell.

In another embodiment, the cancer cell contacted with riluzole is further contacted with an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, or a combination thereof.

In a certain embodiment, the chemotherapeutic agent is selected from the group consisting of 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine[1,1-cyclobutane-dicarboxylato (2-)-0,0']-,(SP-4-2) (carboplatin); and 5β,20-Epoxy-1,2α,4,7β,10β,13α-hexahydroxytax-1-1-en-9-one 4,10-diacetate 2-benzoate 13-ester with (2R,3S)—N-benzoyl-3-phenylisoserine (paclitaxel).

In further embodiment, the B-raf inhibitor is 4-(4-{3-[4-chloro-3-(trifluoromethyl)phenyl]ureido}phenoxy)-N2-methylpyri-dine-2-carboxamide 4-methylbenzenesulfonate (sorafenib).

In an additional embodiment, the anti-apoptosis inhibitor is a Bcl-2 inhibitor.

In yet another embodiment, the benzoquinone ansamycin antibiotic is geldanamycin or 17-N-allylamino-17-demethoxygeldanamycin.

In another certain embodiment, the anti-angiogenesis agent is bevacizumab.

In various other embodiments, the present invention contemplates, in part, a method for reducing growth of a glutamate-releasing and/or GRM1 expressing tumor in a subject by administering to the subject an effective amount of 2-amino-6-trifluoromethoxybenzothiazole (riluzole), thereby reducing tumor cell growth, proliferation, and/or metastasis.

In a particular embodiment, the glutamate-releasing tumor is selected from the group consisting of: melanoma, colon adenocarcinoma, breast carcinoma, thyroid carcinoma, lung carcinoma, glioma, neuroblastoma, and lymphoma.

In a particular embodiment, the tumor is selected from the group consisting of: colon adenocarcinoma, breast carcinoma, thyroid carcinoma, lung carcinoma, glioma, neuroblastoma, and lymphoma.

In one embodiment, the tumor is a GRM1 expressing tumor.

In another particular embodiment, the subject is further administered an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, or a combination thereof.

In a certain embodiment, the chemotherapeutic agent is selected from the group consisting of 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine[1,1-cyclobutane-dicarboxylato (2-)-0,0']-,(SP-4-2) (carboplatin); and 56,20-Epoxy-1,2α,4,7β,10β,13α-hexahydroxytax-1-1-en-9-one 4,10-diacetate 2-benzoate 13-ester with (2R,3S)—N-benzoyl-3-phenylisoserine (paclitaxel).

In another certain embodiment, the B-raf inhibitor is 4-(4-{3-[4-chloro-3-(trifluoromethyl)phenyl]ureido}phenoxy)-N2-methylpyri-dine-2-carboxamide 4-methylbenzene-sulfonate (sorafenib).

In another certain embodiment, the anti-apoptosis inhibitor is a Bcl-2 inhibitor.

In another certain embodiment, the benzoquinone ansamycin antibiotic is geldanamycin or 17-N-allylamino-17-demethoxygeldanamycin.

In another certain embodiment, the anti-angiogenesis agent is bevacizumab.

In a particular embodiment, the riluzole is administered prior to surgical excision of at least a portion of the melanoma.

In another particular embodiment, the riluzole is administered following surgical excision of at least a portion of the melanoma.

In another particular embodiment, the riluzole is administered in a chronic dose.

In another particular embodiment, the riluzole is administered orally, intravenously, or intraperitoneally.

DETAILED DESCRIPTION

Figure 1:
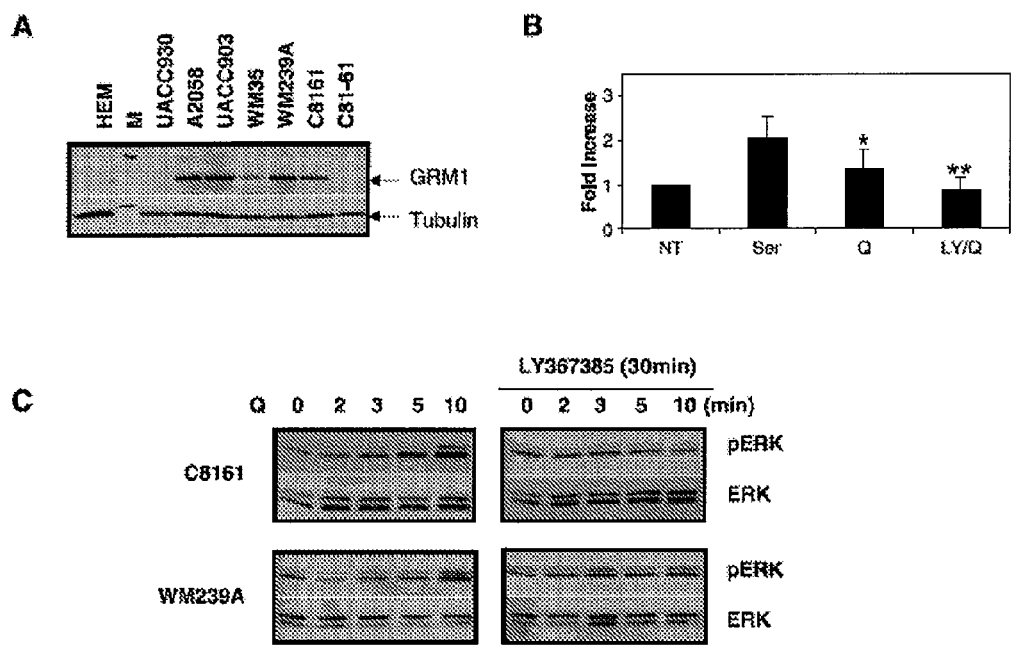
FIG. 1A is an immunoblot for detecting GRM1 protein expression in several human melanoma cell lines.
FIG. 1B is a graph depicting the results of GRM1 agonist-induced IP3 accumulation.
FIG. 1C is an immunoblot demonstrating that stimulation of GRM1 in human melanoma cell lines led to the activation of ERK.

Glutamate is the predominant excitatory neurotransmitter in the mammalian central nervous system, and it can signal through a variety of glutamate receptors. Although once thought to be restricted to the central nervous system, glutamate signaling has been shown in a variety of non-neuronal tissues, including bone and skin (Skerry and Genever (2001) *Trends Pharmacol. Sci.* 22:174-181). There are two main categories of glutamate receptors. The ionotropic receptors are glutamate-gated, cation-specific ion channels, whereas the metabotropic receptors are coupled to intracellular signal-transduction pathways through G proteins. Metabotropic glutamate receptors are members of the large family of seven-transmembrane-domain G protein-coupled receptors. Both glutamate receptor, metabotropic 1 (Grm1) and glutamate receptor, metabotropic 5 (Grm5) (also called Gprc1 and mgluR5) are group 1 metabotropic glutamate receptors coupling primarily to phosphoinositide hydrolysis. Grm1 has also been shown to couple to multiple intracellular signaling cascades including adenylate cyclase activation (Hermans and Chaliss (2001) *Biochem. J.* 359:465-484).

The present invention generally provides methods for reducing, decreasing, and/or inhibiting the growth of a glutamate-releasing tumor using the glutamate release inhibitor and Grm1 antagonist, 2-amino-6-trifluoromethoxybenzothiazole (riluzole).

In various embodiments, the present invention provides a method to reduce cancer cell growth, proliferation, and/or metastasis by contacting the cancer cell with riluzole. As used herein, the terms "reduce," "suppresses," "decreases," "inhibits", "represses," "lowers," "abates," or "lessens" relate generally to the ability of an amount of riluzole to cause a relevant, but smaller magnitude of physiological or cellular response, such as in tumor cell growth, proliferation, and/or metastasis as measured according to routine techniques in the diagnostic art. Specific examples of relevant responses include reduced size, mass, or volume of a tumor, reduced MAPK signaling, reduced phosphor-ERK1/2, reduction in cell number, and reduced cancer cell migration, i.e., metastasis.

Other exemplary responses include reduced levels of activated components of cellular signaling pathways, including but not limited to members of the Ras/Raf-1/MEK/ERK pathways.

Other relevant physiological or cellular responses (in vivo or in vitro) will be apparent to persons skilled in the art. A "decreased" or "reduced" response can be a "statistically significant" decreased or reduced amount compared to the response produced by a control composition, and can include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. Tumor cells can be primary tumor cells or metastatic tumor cells.

Particular examples of glutamate-releasing tumors include, but are not limited to, melanoma, colon adenocarcinoma, breast carcinoma, thyroid carcinoma, lung carcinoma, glioma, neuroblastoma, and lymphoma.

The present invention, contemplates, in part, that cancer cells can be screened for GRM1 expression and/or glutamate-releasing properties prior to treatment. For example, a clinician can perform a biopsy and assay the tissue sample for GRM1 mRNA (e.g., by RT-PCR, Northern blot, and the like) and/or protein expression (e.g., by immunoassay, Western blot, and the like), and for the release of glutamate using routines that are known and commonly practiced in the art. Cancer cells that show an increase in GRM1 expression and/or glutamate release compared to normal or non-cancerous tissue are suitable for treatment with the glutamate release inhibitor and Grm1 antagonist, riluzole.

The term "melanoma" as used herein includes all types of melanoma, including, for example, melanoma skin cancer, ocular melanoma, and mucosal melanoma.

In particular embodiments, cancer cells are contacted with an effective amount of riluzole in order to achieve the desired effect. As used herein, the term "effective amount" refers to an amount effective, at dosages and for periods of time necessary, to achieve the desired result. In some embodiments, the desired result in a therapeutic or prophylactic result.

A "therapeutically effective amount" of riluzole may vary according to factors such as the disease state, age, sex, and weight of the individual, and the ability of riluzole to elicit a desired response in the individual. A therapeutically effective amount is also one in which any toxic or detrimental effects of riluzole are outweighed by the therapeutically beneficial effects. The term "therapeutically effective amount" refers to an amount of riluzole or composition comprising the same, which is effective to treat a disease or disorder in a mammal (e.g., a patient).

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

In various other embodiments, the present invention provides a method to induce apoptosis in a cancer cell by contacting the cancer cell with riluzole, thereby inhibiting cancer cell growth, proliferation, and/or metastasis.

As used herein, the terms "enhance," "increase," "stimulate," "facilitate," "promote," and "heightens," refer generally to the ability of riluzole to produce or cause a larger magnitude of physiological response (i.e., downstream effects) in a cell, as compared to the response caused by a control molecule/composition. A measurable physiological response may include, for example, increased cell-killing activity of a cytotoxic agent towards a cancer cell, increased tumor cell apoptosis, improvements in cancer-related symptoms, and others apparent from the understanding in the art and the description herein. An "increased" or "enhanced" amount is typically a "statistically significant" amount, and can include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the amount produced by a control composition.

As used herein, the term "apoptosis" refers to the killing of a cell by activation of a programmed cell death pathway. Indicators of apoptosis can be characterized by distinct morphologic changes consisting of cell shrinkage, nuclear condensation, and internucleosomal DNA fragmentation. Preferably, in one embodiment, the indicator of apoptosis is a biochemical indicator of apoptosis. For example, biochemical indicators of apoptosis may monitor caspase-8 activity, which is induced predominantly from apoptotic stimuli received via integral membrane death receptors such as Fas and TNFR1.

In another embodiment, biochemical indicators of apoptosis initiated from mitochondria may be assayed, such as caspase-9 activity or cytochrome C release. Alternatively, rather than monitoring apoptosis from a single pathway, a particular embodiment monitors the common effector of different apoptosis pathways, for example, caspase-3 activity. It has been established in the art that once activated, both caspases 8 and 9 participate in a cascade that culminates in the activation of caspase-3, which cleaves several substrates, resulting in chromosomal DNA fragmentation and cellular morphologic changes characteristic of apoptosis. Thus, it would be understood by one ordinarily skilled in the art that when the in vitro indicator of nephrotoxicity monitors caspase-3 activity, effectively all apoptotic pathway are being monitored.

In various other embodiments, the present invention provides a method for reducing growth of a glutamate-releasing tumor in a subject by administering to the subject an effective amount of riluzole. In particular embodiments, the present invention provides methods for inhibiting growth of a glutamate-releasing tumor in a subject by administering to the subject a therapeutically effective amount of riluzole. In certain embodiments, the present invention provides methods for treating a subject having a glutamate-releasing tumor by administration to the subject of a therapeutically effective amount of riluzole.

The term "subject" as used herein includes, but is not limited to, an organism; a mammal, including, e.g., a human, non-human primate (e.g., baboon, orangutan, monkey), mouse, pig, cow, goat, dog, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate. In preferred embodiments, the subject is human. In particular embodiments, the subject is a patient.

A subject includes those mammals diagnosed with a GRM1 expressing and/or glutamate-releasing cancer, including but not limited to, colon adenocarcinoma, breast carcinoma, thyroid carcinoma, lung carcinoma, glioma, neuroblastoma, and lymphoma. In particular embodiments, a subject is prescreened for a tumor or cancer cell that expresses GRM1 or has glutamate-releasing properties. In related embodiments, a screened subject having a tumor that expresses GRM1 or has glutamate-releasing properties is treated with the methods of the present invention.

"Treat," "Treatment," or "treating," as used herein, includes any desirable effect on the symptoms or pathology of a disease or condition associated with glutamate-releasing tumors (e.g., reducing tumor growth), or a risk of developing such a condition, and may include even minimal changes or improvements in one or more measurable markers of disease or condition being treated. "Treatment" or "treating" does not necessarily indicate complete eradication or cure of the disease or condition, or associated symptoms thereof. The subject receiving this treatment is any animal in need, including primates, in particular humans, and other mammals such as equine, bovine, sheep, goat, porcine, canine, feline, rat, guinea pig, and mouse and non-mammals such as chicken. Exemplary markers of clinical improvement include decreased tumor size, symptomatic improvements (e.g., increased energy levels, decreased pain or discomfort), decreased chemoresistance (e.g., decreased tumor size in response to primary chemotherapy), as described herein and known in the art.

In various embodiments described herein, a cancer cell is contacted with a composition comprising an amount of riluzole and one or more of a GRM1 antagonist, an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, or a combination thereof. In certain embodiments, a cancer cell is contacted with a composition comprising an amount of riluzole and one or more of a GRM1 antagonist, an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, and other agents known to treat cancer or a combination thereof.

Preferably, the GRM1 antagonist is a competitive or non-competitive GRM1 antagonist. In one embodiment, the GRM1 antagonist is a competitive or noncompetitive GRM1 antagonist. As used herein the term "competitive antagonist" refers to an antagonist that binds to the same site as the natural ligand glutamate. A preferred competitive antagonist is LY367385. As used herein the term "noncompetitive antagonist" refers to an antagonist that binds to the transmembrane domain of the receptor resulting in stabilization of inactive conformation. A preferred noncompetitive antagonist is BAY36-7620.

Exemplary chemotherapeutic agents include, but are not limited to, 3,4-dihydro-3-methyl-4-oxoimidazo[5,1-d]-astetrazine-8-carboxamide (temozolomide); 5-(3,3-dimethyl-1-triazeno)-imidazole-4-carboxamide (dacarbazine); platinum, diammine[1,1-cyclobutane-dicarboxylato (2-)-0,0']-, (SP-4-2) (carboplatin); and 5β,20-Epoxy-1,2α,4,7β,10β,13β-hexahydroxytax-11-en-9-one 4,10-diacetate 2-benzoate 13-ester with (2R,3S)—N-benzoyl-3-phenylisoserine (paclitaxel).

Exemplary B-raf inhibitors include but are not limited to, PLX4032; PLX4720; R7204; RAF265 (Smalley and Flaherty (2009) *Future Oncology*, Volume 5, Number 6, pp. 775-778), and 4-(4-{3-[4-chloro-3-(trifluoromethyl)phenyl]ureido}phenoxy)-N2-methylpyridine-2-carboxamide 4-methylbenzenesulfonate (sorafenib).

Exemplary anti-apoptosis inhibitors include, but are not limited to, inhibitors of the inhibitor of apoptosis protein (IAP), survivin, and Bcl-2.

Exemplary benzoquinone ansamycin antibiotics include, but are not limited to geldanamycin and 17-N-allylamino-17-demethoxygeldanamycin.

Exemplary anti-angiogenesis agents include, but are not limited to bevacizumab.

Additional exemplary agents that are effective in treating cancer and that can be used in compositions of the present invention include, but are not limited to, Exemplary chemotherapeutic or cytotoxic agents suitable for use in particular embodiments of the present invention include, but are not limited to: chemotherapeutic agents include alkylating agents such as thiotepa and CYTOXAN® cyclophosphamide; alkyl sulfonates such as busulfan, improsulfan and piposulfan;

aziridines such as benzodopa, carboquone, meturedopa, and uredopa; ethylenimines and methylamelamines including altretamine, triethylenemelamine, trietylenephosphoramide, triethiylenethiophosphoramide, and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfanide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; cyclosporine, sirolimus, rapamycin, ibandronate; topoisomerase inhibitor RFS 2000; difluoromethylornithine (DMFO); retinoids such as retinoic acid; CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU, leucovovin; anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other antiandrogens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

Other compounds that are effective in treating cancer are known in the art and described herein that are suitable for use with the compositions and methods of the present invention are described, for example, in the "Physicians Desk Reference, $62^{nd}$ edition. Oradell, N.J.: Medical Economics Co., 2008", Goodman & Gilman's "The Pharmacological Basis of Therapeutics, Eleventh Edition. McGraw-Hill, 2005", "Remington: The Science and Practice of Pharmacy, 20th Edition. Baltimore, Md.: Lippincott Williams & Wilkins, 2000.", and "The Merck Index, Fourteenth Edition. Whitehouse Station, N.J.: Merck Research Laboratories, 2006", incorporated herein by reference in relevant parts Riluzole and other agents may be administered in a single composition or dosage form. According to the methods of the present invention, the composition is administered locally or systemically to a patient in need thereof. In practice, a composition containing riluzole may be administered in any variety of suitable forms, for example, by inhalation, topically, parenterally, rectally, or orally. More specific routes of administration include intravenous, intramuscular, subcutaneous, intraocular, intrasynovial, colonical, intraperitoneal, intravaginally, transepithelial including transdermal, ophthalmic, sublingual, buccal, dermal, ocular, nasal inhalation via insufflation, and aerosol.

The glutamate release inhibitor, GRM1 antagonist, and other agents may be administered in a single composition or dosage form or each compound may be independently administered in separate compositions. Separate compositions may be administered simultaneously or sequentially.

According to the methods of the present invention, the composition is administered systemically to a patient in need thereof. Systemic delivery may be accomplished through, for example, oral or parenteral administration.

A composition containing riluzole may be presented in forms permitting administration by the most suitable route.

The choice of vehicle is generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, riluzole may be incorporated into sustained-release preparations and formulations.

More specific routes of administration include intravenous, intramuscular, subcutaneous, intrasynovial, intraperitoneal, transmucosal, and transepithelial including transdermal and sublingual.

For parenteral administration, emulsions, suspensions or solutions of one or more active agents (e.g., glutamate release inhibitor, GRM1 antagonist, anti-proliferative agent, chemotherapeutic agent, B-raf inhibitor, Bcl-2 inhibitor, etc.) in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the glutamate release inhibitor and/or GRM1 antagonist as a free base or pharmacologically acceptable salt can be prepared in water suitably mixed with a surfactant such as hydroxypropyl-cellulose. Dispersions can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating one or more active agents in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing riluzole may be used. Riluzole may be also incorporated in a gel or matrix base for application in a patch, which would allow a controlled release of compound through transdermal barrier.

For administration by inhalation, riluzole may be dissolved or suspended in a suitable carrier for use in a nebulizer or a suspension or solution aerosol, or may be absorbed or adsorbed onto a suitable solid carrier for use in a dry powder inhaler.

Another embodiment of the invention provides for riluzole to be administered by means of perfusion balloons. These perfusion balloons, which make it possible to maintain a blood flow and thus to decrease the risks of ischemia of the myocardium, on inflation of the balloon, also enable the compound to be delivered locally at normal pressure for a relatively long time, more than twenty minutes, which may be necessary for its optimal action. Alternatively, a channeled balloon catheter ("channeled balloon angioplasty catheter", Mansfield Medical, Boston Scientific Corp., Watertown, Mass.) may be used. The latter consists of a conventional balloon covered with a layer of 24 perforated channels, which perfuse via an independent lumen through an additional infusion orifice.

Various types of balloon catheters, such as double balloon, porous balloon, microporous balloon, channel balloon, balloon over stent and hydrogel catheter, all of which may be used to practice the invention, are disclosed in Reissen et al. (1994), the entire contents of which are hereby incorporated by reference.

The use of a perfusion balloon catheter is especially advantageous; as it has the advantages of both keeping the balloon inflated for a longer period of time by retaining the properties of facilitated sliding and of site-specificity of the hydrogel are gained simultaneously.

One or more active agents may be also incorporated in a gel or matrix base for application in a patch, which would allow a controlled release of compound through transdermal barrier.

The percentage of one or more active agents in the compositions used in the present invention may be varied, it being necessary that it should constitute a proportion such that a suitable dosage shall be obtained. The amount of active agent to produce a single dosage form will generally be that amount of the ingredient which produces a therapeutic effect. Generally, out of one hundred percent, this amount will range from about 0.1 percent to about 99 percent of active ingredient, about 1 percent to about 90 percent of active ingredient, about 10 percent to about 80 percent of active ingredient, about 25 percent to about 75 percent of active ingredient, about 30 percent to about 70 percent of active ingredient, about 40 percent to about 60 percent of active ingredient, or about 50 percent of active ingredient.

In another embodiment, the amount of active ingredient in a single dosage from that is required to produce a therapeutic effect is about 0.1% active ingredient, about 1% active ingredient, about 5% active ingredient, about 10% active ingredient, about 15% active ingredient, about 20% active ingredient, about 25% active ingredient, about 30% active ingredient, about 35% active ingredient, about 40% active ingredient, about 45% active ingredient, about 50% active ingredient, about 55% active ingredient, about 60% active ingredient, about 65% active ingredient, about 70% active ingredient, about 75% active ingredient, about 80% active ingredient, about 85% active ingredient, about 90% active ingredient, or about 95% active ingredient or more.

Several unit dosage forms may be administered at about the same time. A dose employed may be determined by a physician or qualified medical professional, and depends upon the desired therapeutic effect, the route of administration and the duration of the treatment, and the condition of the patient.

The terms "acute dose" or "acute administration" of one or more active agents mean the scheduled administration of the active agent(s) to a patient on an as-needed basis at a dosage level determined by the attending physician to elicit a relatively immediate desired reaction in the patient, given the patient's age and general state of health.

A "sub-acute dose" is a dose of the active agent(s) at a lower level than that determined by the attending physician to be required for an acute dose, as described above. Sub-acute doses may be administered to the patient on an as-needed basis, or in a chronic, or on-going dosing regimen.

The terms "chronic dose" or "continuous administration" of the active agent(s) mean the scheduled administration of the active agent(s) to the patient on an on-going day-to-day basis.

In the adult, the doses are generally from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention. The maximum dosage amount tolerated by the patient is preferred.

Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active agent(s) may be administered 1 to 4 times per day. Of course, for other patients, it will be necessary to prescribe not more than one or two doses per day.

Compositions comprising an amount of riluzole and one or more of a GRM1 antagonist, an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, and other agents known to treat cancer or a combination thereof can be administered during any stage (e.g. early, middle, or advanced) of tumorigenesis. In one embodiment, a composition as described herein, is administered prior to surgical excision of at least a portion of the tumor. In another embodiment, a composition of the invention is administered following surgical excision of at least a portion of the tumor. Additionally, a composition comprising an amount of riluzole and one or more of a GRM1 antagonist, an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, and other agents known to treat cancer or a combination thereof can be administered in a chronic dose, for example, following an initial course of therapy.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Materials and Methods

Antibodies and Reagents.

Anti-phosphorylated ERK, anti-ERK, and anti-poly(ADP-ribose) polymerase (PARP) antibodies were purchased from Cell Signaling (Danvers, Mass.); anti-GRM1 antibodies were purchased from BD Biosciences (Franklin Lakes, N.J.) and ImmunoStar, Inc. (Hudson, Wis.); and monoclonal αα-tubulin antibody, myoinositol, and riluzole were obtained from Sigma (St. Louis, Mo.). DMSO was purchased from Fisher Scientific (Pittsburgh, Pa.). L-quisqualate[(L)-(+)-a-amino-3,5-dioxo-1,2,4-oxadiazolidine-2-propanoic acid], LY367385 [(S)-(+)-α-amino-4-carboxy-2-methylbenzeneacetic acid], and JNJ16259685 were purchased from Tocris (Ellisville, Mo.). BAY36-7620 [(3aS,6aS)-6a-naphtalen-2-ylmethyl-5-methyliden-hexahydro-cyclopental[c]-furan-1-on] was obtained from Bayer (West Haven, Conn.).

Cell Culture.

Primary human epidermal melanocytes (HEM) were purchased from Cascade Biologics (Portland, Oreg.) and maintained in Medium 254 and human melanocyte growth supplements. UACC930, UACC903, and A2058 were provided by Dr. Jeffrey M. Trent (Translational Genomics Research Center, Phoenix, Ariz.). WM239A and WM35 were from Dr. Meenhard Herlyn (Wistar Institute, Philadelphia, Pa.). C8161 and C81-61 were from Dr. Mary J. C. Hendrix (Children's Memorial Research Center, Chicago, Ill.). Melanoma cells were grown in RPMI 1640 plus 10% fetal bovine serum (FBS). For glutamate measurement or induction experiments with GRM1 agonist, customized glutamine- and glutamate-free RPMI 1640 (Invitrogen-Life Technologies, Carlsbad, Calif.) was used with 10% dialyzed FBS (Invitrogen-Life Technologies) and supplemented with 2 mmol/L GlutaMax (Invitrogen-Life Technologies) to minimize glutamate in the medium. For the measurement of inositol-1,4,5-triphosphate (IP3), customized glutamine- and glutamate-free RPMI 1640 was additionally deprived of inositol (Invitrogen-Life Technologies).

Western Immunoblots.

Protein lysates were prepared as described in K. A. Cohen-Solal et al., "Progressive appearance of pigmentation in amelanotic melanoma lesions," Pigment Cell Res. 15:282-9 (2002). Cells were washed with ice-cold PBS. Extraction buffer was added and cells were collected. After incubation on ice for 20 minutes, supernatants were collected by centrifugation at 4° C. Protein concentration was determined using the DC protein assay kit (Bio-Rad, Hercules, Calif.). Routinely, 25 µg of protein lysates were loaded for Western immunoblots.

IP3 Measurements.

After overnight incubation in the presence of 3 µCi of myo-[$^{3H}$]inositol (3.22 TBq/mmol; GE Healthcare, Piscataway, N.J.), cells were incubated in fresh glutamate/inositol/serum-free RPMI 1640 with LiCl (10 mmol/L) for 15 minutes in the presence or absence of LY367385 (10 µmol/L) before stimulation with L-quisqualate (10 μmol/L) for 15 min. The reactions were terminated and samples were either washed with the addition of 1 mL of a 1:1 mixture of 1,1,2-trichlorotrifluoroethane (Sigma) and tri-n-octalamine (Sigma) or washed twice with water-saturated diethyl ether (Sigma). Levels of incorporated $^{3H}$]inositol in IP3 were measured by a scintillation counter (Beckman Coulter, Inc., Fullerton, Calif.).

DNA Transfection.

Transfections of DNA were done with N-[1-(2,3-dioleoyloxyl)propyl]-N,N,N,-trimethylammoniummethyl sulfate liposomal transfection reagent (Roche, Basel, Switzerland) according to the manufacturer's instructions. Dominant-negative GRM1 (dnGRM1) constructs were provided by Dr. Anna Francesconi (Albert Einstein College of Medicine, Bronx, N.Y.). DNA transfections were done with 0.5 μg of DNA per 60-mm plate.

3-(4,5-Dimethylthiazol-2-yl)-2,5-diphenyltetrazolium Bromide Cell Proliferation Assays.

3-(4,5-Dimethylthiazol-2-yl)-2,5-diphenyltetrazolium bromide (MU) assays were done according to the manufacturer's protocol (Roche). Briefly, $10^3$ cells were plated in 96-well plate and treated with various compounds as indicated. Absorbance was measured by GENios plate reader (Tecan, Durham, N.C.) for the time points indicated.

Measurement of Extracellular Glutamate.

Amplex Red Glutamic Acid/Glutamate Oxidase assay kit (Invitrogen-Molecular Probes) was used to measure the amount of glutamate released in the medium. Cells were grown in medium devoid of glutamate and glutamine but supplemented with GlutaMax (2 mmol/L) for 3 days. Cells were plated at $10^3$ cells per well with 200 μL of medium containing specific compounds with concentration as indicated in 96-well plate. After specified times, 100 μL of medium was collected for measurement of the amount of glutamate released according to the manufacturer's protocol. Cells left with ~100 μL of medium in the wells were used to confirm the viability of cells by MTT cell proliferation assays.

Cell Cycle Analysis.

Cells were plated at $2 \times 10^6$ per 100-mm culture plate and treated as indicated. After 24 and 48 h, cells were collected and washed twice with ice-cold PBS. Cell pellets were fixed by drop-wise addition of ice-cold 70% ethanol and incubated for 20 minutes at 4° C. Fixed cells were washed twice with ice-cold PBS and resuspended in 500 μL PBS. Cells were treated with RNase A solution (20 μg/mL; Sigma) and labeled with propidium iodide (50 μg/mL; Sigma) for 30 minutes. Cell cycle analysis was done by the Flow Cytometry Facility Core at Rutgers University (Piscataway, N.J.) using a Beckman Coulter system (Epics XL-MCL model).

Xenografts in Immunodeficient Nude Mice.

All animal studies were approved by the Institutional Review Board for the Animal Care and Facilities Committee of Rutgers University. Nude mice were purchased from Taconic (Hudson, N.Y.). Human melanoma cells, C8161, were injected into the dorsal area at $10^6$ cells per site. Tumor size was measured twice weekly with a Vernier caliper and calculated as described in A. Stepulak et al., "NMDA antagonist inhibits the extracellular signal-regulated kinase pathway and suppresses cancer growth," Proc. Nat'l Acad. Sci. U.S.A. 102:15605-10 (2005). Treatment with either vehicle (DMSO) or 7.5 mg/kg riluzole was given daily via p.o. gavage or i.v. when tumor volumes reached 6 mm$^3$. After 18 days of treatment, experiments were terminated due to tumor burden, as tumor volume had reached 300 mm$^3$ in some animals.

Example 1

Functional GRM1 in Human Melanoma Cells

Previous analyses of several human melanoma cell lines and biopsies showed that approximately 40% of them were positive for GRM1 expression. An example of immunoblots of several human melanoma cell lines and normal primary HEMs is shown in FIG. 1A. HEM was used as a normal melanocyte control, and α-tubulin was used as a loading control. Expression of GRM1 was detected in some human melanoma cell lines but not in HEM.

MAPK is one of the key signaling pathways in human melanoma. Therefore, a study was conducted to determine if the MAPK pathway is also critical in GRM1-positive human melanoma cells. It is well known that the common BRAF-activating mutation (V600E) constitutively stimulates MAPK signaling. Therefore, genotypes of BRAF and N-Ras were assessed by DNA sequencing in GRM1-positive human melanoma cell lines. C8161 did not have the most common mutations at either BRAF (codon 600) or N-Ras (codons 12, 13, and 61). However, WM239A displayed a mutation in BRAF (V600D). Most of the other cell lines showed the most common BRAF mutation (V600E; data not shown). In human melanoma cell lines that bore the most common activating mutation in BRAF (V600E), such as UACC903, MAPK pathway was constitutively activated. As a consequence, stimulation with GRM1 agonist did not lead to further activation of ERK (data not shown). Therefore, cell lines bearing the V600E BRAF mutation were excluded from further studies. C8161 and WM239A were selected for subsequent analysis of the involvement of GRM1 signaling in human melanoma.

To examine the functionality of GRM1 in C8161 and WM239A, the cells were stimulated with GRM1 agonist, L-quisqualate (Q), and the accumulation of IP3 was measured (FIG. 1B). The human melanoma cell lines (C8161 and WM239A) were stimulated with L-quisqualate alone (10 μmol/L; Q) for 15 minutes or pretreated with LY367385 (10 μmol/L) for 15 minutes followed by stimulation with L-quisqualate (LY/Q) for 15 minutes. In FIG. 1B, data is expressed relative to no treatments (NT). FBS (10%) was used as a positive control (Ser). Columns represent the average of three independent experiments of a representative cell line (WM239A); bars, SD. *, P<0.05, compared with no treatment (t test); **, P<0.05, compared with L-quisqualate (t test).

Cells were divided into four groups: no treatment, serum as a positive control, treatments with group I mGluR agonist (L-quisqualate), or preincubation with GRM1-specific antagonist, LY367385, followed by induction with L-quisqualate. To minimize the amount of glutamate, the natural ligand of GRM1, glutamate- and glutamine-free media were used for the measurement of IP3 supplemented with GlutaMax. Three independent experiments with C8161 and WM239A human melanoma cell lines were conducted, and representative data are shown. In the presence of serum, an increase in levels of IP3 accumulation was detected when compared with no treatment.

Treatment with GRM1 agonist (L-quisqualate) for 15 minutes resulted in a statistically significant increase in the accumulation of IP3. The specificity of L-quisqualate-induced increase in IP3 accumulation was shown by the absence of IP3 accumulation when these cells were pretreated with GRM1 antagonist (LY367385) followed by induction with L-quisqualate. The functionality of GRM1 in these human melanoma cells was further confirmed by GRM1 agonist-induced ERK phosphorylation (FIG. 1C). L-quisqualate-induced ERK activation was inhibited when these cells were pretreated with LY367385 for 30 minutes before induction with L-quisqualate. Taken together, these results show that GRM1 receptors in these human melanoma cell lines were functional and responded to GRM1 agonist and antagonist.

Example 2

Induction of Apoptosis by dnGRM1

Figure 2:
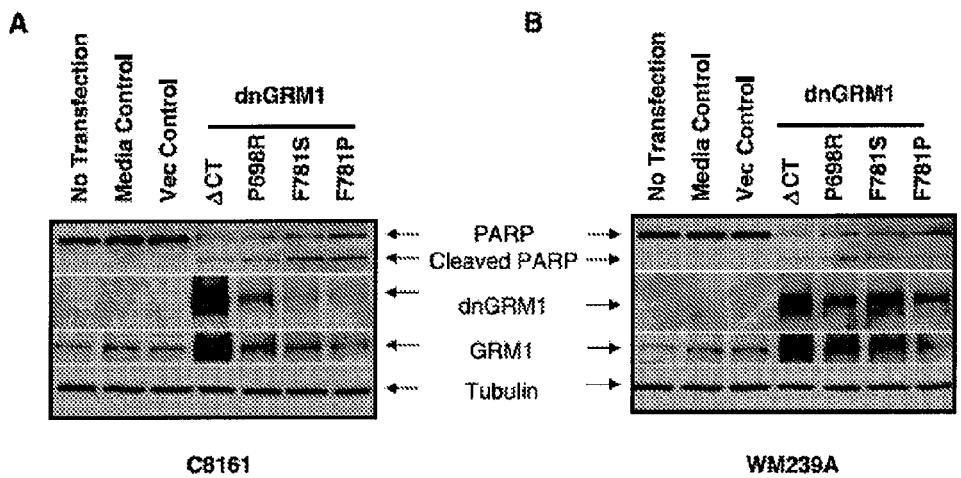
FIGS. 2A and B are immunoblots showing dnGRM1 induced apoptosis in C8161 (A) and WM239A (B)

To further investigate GRM1 functionality and activity in human melanoma cells, two different but complimentary means were used to suppress GRM1 function. First, dnGRM1 was studied. These mutants have a small deletion (DCT 694-695, DCT) or single base substitutions (P698R, F781S, and F781P) in the intracellular loop 2 or 3, which had been shown to be critical in GRM1 signaling. Human melanoma cell lines C8161 (FIG. 2A) and WM239A (FIG. 2B) were transfected with vector control or four different dnGRM1 mutants. At 24 hours after transfection, protein lysates were collected for Western immunoblots. PARP cleavage is a well-known apoptotic marker by the appearance of the cleaved form at 89 kDa. PARP cleavage was detected only in dnGRM1-transfected samples but not in vector control (FIG. 2, top). Second panels show the levels of exogenously transfected GRM1 to verify the presence of dnGRM1 in these cells. dnGRM1 clones were made from a wild-type GRM1 cDNA from rat brain. Therefore, anti-GRM1 antibody that only recognizes the rodent forms of GRM1 was used. Apoptotic marker was only observed in samples that had been transfected with dnGRM1.

Example 3

Inhibition of Human Melanoma Cell Proliferation by GRM1 Antagonists

As a second approach, GRM1 antagonists were used to examine GRM1 functionality and activity in human melanoma cells. LY367385, a competitive antagonist, binds to the same site as the natural ligand glutamate. BAY36-7620, one of the noncompetitive antagonists, binds to the transmembrane domain of the receptor resulting in stabilization of inactive conformation. MTT cell proliferation assays were used to assess growth response of human melanoma cells in the presence of competitive or noncompetitive antagonist.

Figure 3:
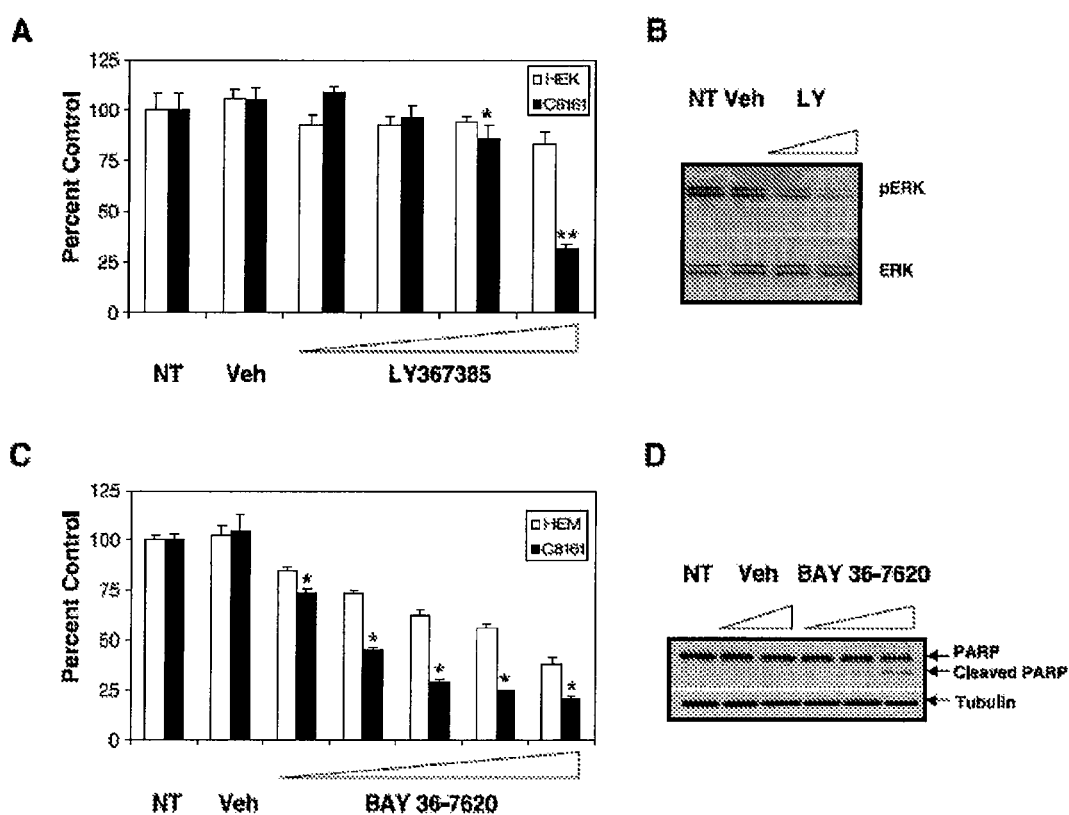
FIG. 3A demonstrates the response of human melanoma cells to LY367385.
FIG. 3B is an immunoblot of ERK phosphorylation after treatments with LY367385 at day 4.
FIG. 3C shows the biological consequences of BAY36-7620 treatments in HEM (white columns) or C8161 (black columns) cells measured by MTT cell viability assays.
FIG. 3D shows Western immunoblots for examining levels of cleaved PARP in C8161 treated with 10, 25, or 50 μmol/L of BAY36-7620 for 48 hours.

Human melanoma cells were grown in the presence of different concentrations of LY367385 in RPMI 1640 devoid of glutamate and glutamine supplemented with GlutaMax because LY367385 competes with the natural ligand glutamate for the binding to GRM1 receptor (FIG. 3A). Cells were treated with LY367385 at concentrations of 10, 50, 100, and 500 µmol/L, respectively. No treatment (NT) and 500 µmol/L NaOH (Veh) were used as controls. Measurement of cell viability/growth was carried out by MIT assays for 4 days. Only measurements on day 4 are shown. Growth of C8161 cells was suppressed in a dose-dependent manner, whereas NaOH virtually had no effect on cell growth (black columns). LY367395 had minimal growth-inhibitory effect on HEK cells (white columns). Bars represent SD. *, $P<0.05$, compared with HEK (t test); **, $P<0.001$, compared with HEK (t test).

The growth of primary HEMs requires special medium supplemented with several growth factors, which contain approximately 70 µmol/L glutamate. In the absence of these factors and glutamate, the growth of HEM was inhibited. Therefore, human embryonic kidney (HEK) cells were used as a normal control instead of HEM. Cell proliferation was measured for 4 days, and the growth of C8161 was inhibited by 70% in the presence of 500 µmol/L LY367385. There was only a negligible effect on the growth of HEK cells at this concentration. In a parallel set of cells under same conditions, protein lysates were prepared and levels of phosphorylated ERK were examined (FIG. 3B). C8161 cells were not treated (NT) or treated with 100 or 500 µmol/L of LY367385 or with 500 µmol/L NaOH (Veh). Protein lysates were prepared for Western immunoblots and probed with phosphorylated ERK. The same membranes were stripped and reprobed with total ERK.

A dose-dependent decrease in levels of phosphorylated ERK was detected in cells treated with 100 or 500 µmol/L of LY367385 in comparison with no treatment or vehicle treated. These results showed that treatment of GRM1-positive human melanoma cells with LY367385, a competitive GRM1 antagonist, resulted in suppression in cell proliferation and that this suppression is likely, in part, due to inhibition of MAPK signaling as indicated by a decrease in levels of activated phosphorylated ERK.

Next, the growth of human melanoma cells was examined in the presence of a GRM1 noncompetitive antagonist, BAY36-7620. As a noncompetitive antagonist, BAY36-7620 does not compete for the binding site with the natural ligand glutamate; therefore, regular growth media were used for both human melanoma cells and HEM. MTT cell proliferation assays were done with different concentrations of BAY36-7620 (10-50 µmol/L) for 4 days (only data for day 4 are shown (FIG. 3C)). Bars represent SD; *, $P<0.001$, compared with HEM (t test). In the presence of BAY36-7620, the growth of C8161 cells was suppressed in a dose-dependent manner, whereas vehicle treatment had very little or no effect on cell growth.

At 30 µmol/L BAY36-7620, only 30% of C8161 cells were viable, whereas >60% of HEM cells were viable. Cell cycle analysis indicated that BAY36-7620-treated C8161 cells showed an increase in the sub-$G_1$ phase after 48 hours of treatment, suggesting an induction of apoptosis by BAY36-7620 (data not shown). Protein lysates were prepared under the same conditions, and PARP cleavage was used as an apoptotic marker. Apoptosis was induced by BAY36-7620 at 50 µmol/L after 48 hours as shown by the cleaved form of PARP in comparison with DMSO treated (Veh) or no treatment (NT) (FIG. 3D). The same blot was probed with αα-tubulin to show equal loading.

These data indicated that a noncompetitive antagonist of GRM1, BAY36-7620, inhibited human melanoma cell growth and induced apoptosis, suggesting that GRM1 could be a target in human melanoma therapy.

Example 4

Inhibition of Glutamate Release by GRM1 Antagonists in Human Melanoma Cells

Only 15% inhibition of melanoma cell growth resulted from administration of 100 µmol/L LY367385 to C8161 cells (FIG. 3A), whereas 10 µmol/L LY367385 was sufficient in the suppression of L-quisqualate-induced ERK activation (FIG. 1C). Studies on mouse melanoma cells and mouse melanocytic clones stably expressing GRM1 showed higher levels of released glutamate than normal mouse melanocytes or vector controls. In light of these results, levels of released glutamate by several human melanoma cell lines were examined. Each day, half of the media were collected and the amount of released glutamate was determined. MTT assays were done to ensure that these cells were viable. Again, because HEM, normal human melanocytes, required growth factors as well as glutamate to grow, HEK cells were used as a control. Regardless of whether they express GRM1, all human melanoma cells examined released more glutamate than HEK. In fact, a substantial amount of glutamate was released into the medium, especially by C8161 cells.

Figure 4:
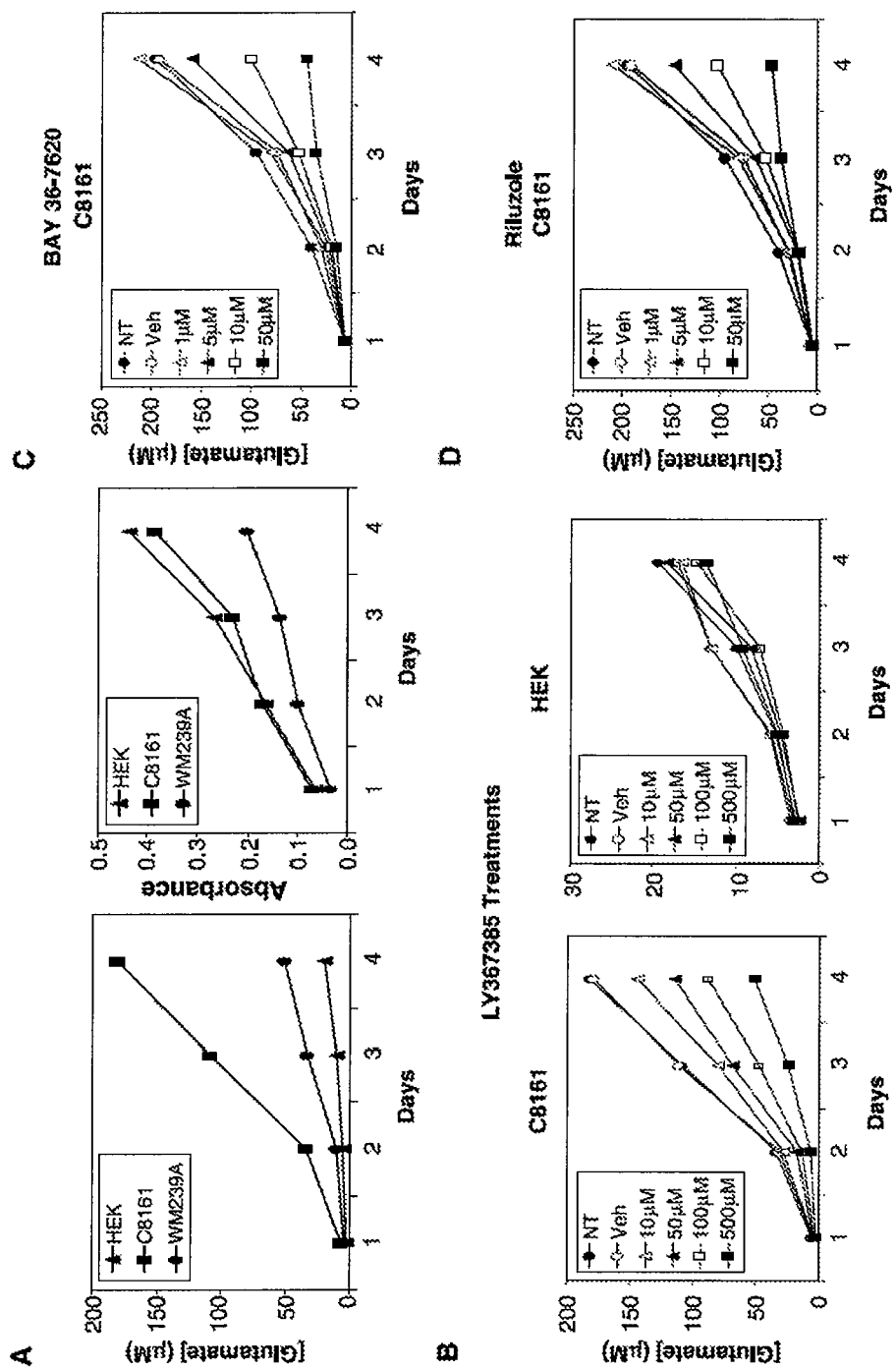
FIG. 4A (left panel) depicts the results of an examination of released glutamate in human melanoma cell lines and HEK cells, and (right panel) depicts MTT cell viability/proliferation assays of a parallel set of cells under the same growth conditions to show the released glutamate was not due to cell death.
FIG. 4B demonstrates the ability of the competitive GRM1 antagonist LY367385 to inhibit the release of glutamate in C8161 and HEK cells at different concentrations for up to 4 days.
FIG. 4C demonstrates that treatment of C8161 cells with BAY36-7620, the noncompetitive GRM1 antagonist, suppressed glutamate release.
FIG. 4D demonstrates that riluzole treatment of C8161 cells suppressed glutamate release.

An example of glutamate released by HEK, C8161, and WM239A is shown (FIG. 4A, left). In FIG. 4A, left, cells were plated in 96-well plates at $10^3$ cells per well and half of the media (100 µL) was collected to measure the amount of glutamate at indicated times. In FIG. 4A, right, cells in the remaining half of the media (100 µL) were subjected to MTT cell proliferation assays. Media without cells was used as a control in each experiment (data not shown). At least three independent experiments were done. After 4 days, C8161 released approximately 200 µmol/L glutamate into the medium, which was about 10 times the amount released by HEK. Although very little glutamate was released by HEK cells, the MTT assay showed their vigorous growth (FIG. 4A, right).

Next, the ability of GRM1 antagonists to inhibit the release of glutamate by these cells was investigated. The vehicle control was 500 µmol/L NaOH. Treatment of C8161 cells with LY367385 resulted in a dose and time-dependent suppression in the levels of released glutamate (FIG. 4B, left). When C8161 cells were treated with 500 µmol/L LY367385, <30% of glutamate was released compared with controls, which correlated with the MU assays. Under the same conditions, very little influence on the glutamate released was detected in LY367385-treated HEK cells (FIG. 4B, right). These results suggested that a higher concentration of LY367385 was required to inhibit GRM1-positive melanoma cell growth due to the constant release of glutamate by these cells. Suppression of glutamate release was also detected in cells treated with BAY36-7620, the noncompetitive GRM1 antagonist (FIG. 4C). DMSO was used as a vehicle control. BAY36-7620 seemed to be more potent in the suppression of glutamate release than LY367385.

Example 5

Inhibition of Cell Proliferation by Glutamate Release Inhibitor Riluzole

Figure 5:
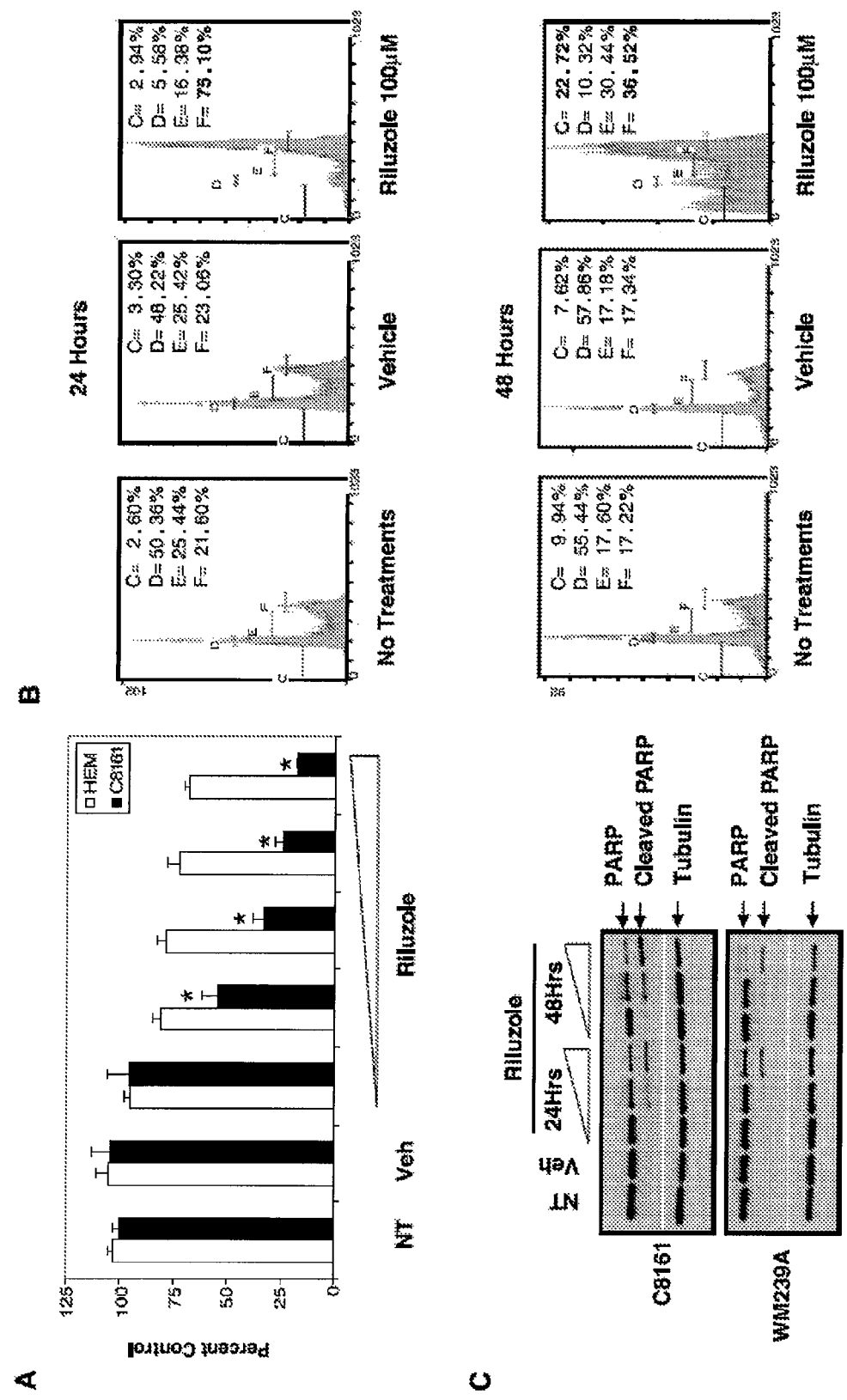
FIG. 5A demonstrates the results of MTT cell proliferation assays used to assess the biological consequences of C8161 (black columns) and HEM (white columns) treated with riluzole.
FIG. 5B demonstrates the results of a cell cycle analysis of C8161 cells treated with riluzole at 24 hours (top) and 48 hours (bottom)
FIG. 5C shows the results of an investigation of the apoptotic response of human melanoma cells to riluzole.

A previous experiment suggested a correlation between levels of released glutamate and cell proliferation (see above). Based on these results, human melanoma cells were treated with riluzole. Riluzole-treated C8161 cells released reduced levels of glutamate (DMSO was used as a vehicle control) (FIG. 4D). Suppression of glutamate release by riluzole also reduced the growth of C8161 human melanoma cells (FIG. 5A). In FIG. 5A, cells were plated on 96-well plate at $10^3$ cells per well and treated with 10, 20, 30, 40, or 50 µmol/L of riluzole. A dose-dependent suppression of C8161 cell growth by riluzole was detected in comparison with no treatment (NT) and DMSO treated (Veh). Only day 4 measurements are shown. Bars represent SD; *, P<0.001, compared with HEM (t test). At 40 µmol/L riluzole, <25% of C8161 cells were viable, whereas >70% of HEM cells were viable, suggesting that HEM cells were less sensitive under similar conditions.

Cell cycle analysis on riluzole-treated C8161 cells showed the accumulation of cells in the $G_2$-M phase at 24 hours (FIG. 5B, top). By 48 hours, there was a substantial increase in cells accumulated in the sub-$G_1$ phase of the cell cycle, suggesting cellular apoptosis (FIG. 5B, bottom). DMSO treatment (Vehicle) had little or no effects. Each phase of cell cycle is indicated as C (sub-$G_1$), D ($G_1$), E (S), and F ($G_2$-M), and the percentage of cells in each phase is given.

To confirm these observations, PARP cleavage was examined by Western immunoblots with C8161 cell lysates prepared at 24 and 48 hours after riluzole treatment (FIG. 5C). Cells were plated and treated with 10, 25, or 50 µmol/L of riluzole for 24 or 48 hours. Protein lysates were extracted for Western immunoblots. After 24 and 48 hours of treatment with 10, 25, and 50 µmol/L of riluzole, cleaved forms of PARP were detected in C8161 compared with no treatment (NT) or DMSO treated (Veh). The same blot was probed with αα-tubulin to show equal loading. Results indicated that treatments with riluzole inhibited growth of human melanoma cells and induced cell cycle arrest leading to apoptosis. These results prompted us to validate the antiproliferative, proapoptotic action of riluzole in human melanoma cells in vivo.

Example 6

Inhibition of Human Melanoma Cell Xenograft Growth by Riluzole

Figure 6:
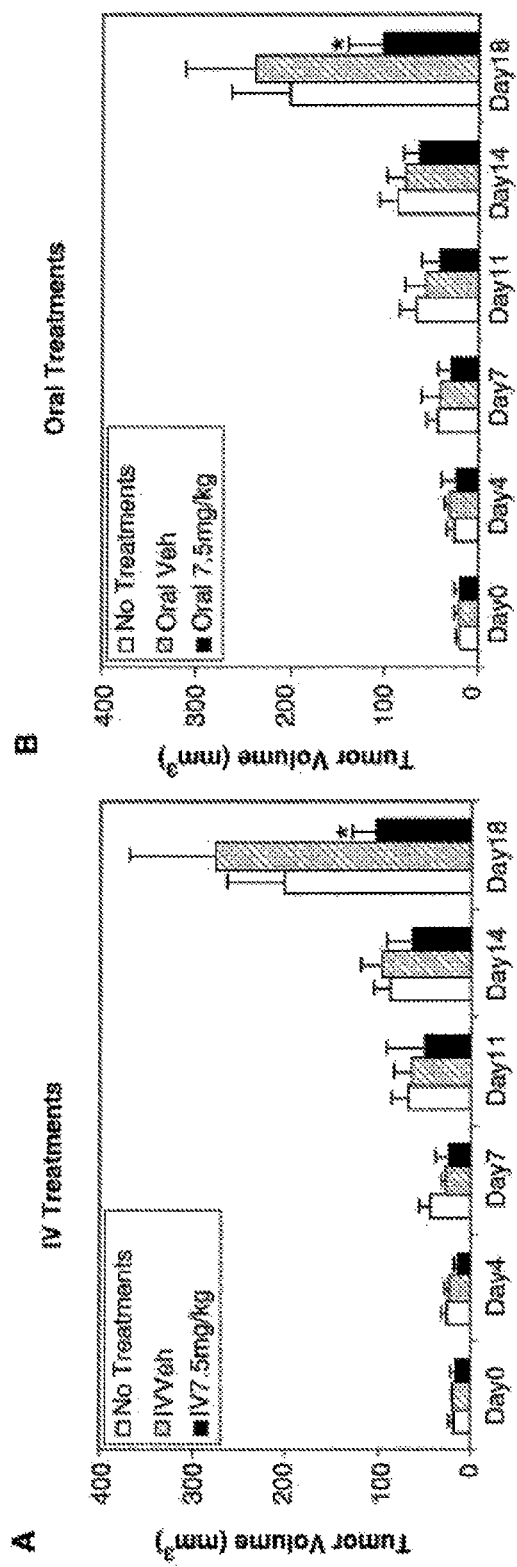
FIGS. 6A and B show the results of an investigation of therapeutic potential of riluzole by C8161 xenograft model.

C8161 cells were inoculated s.c. into nude mice at $10^6$ per site. Based on the experiments done previously by others, the maximum tolerated dose of riluzole was 20 mg/kg. Mice treated with this dose for 2 years had no carcinogenic effects. Based on this information and pilot experiments, mice were treated with 7.5 mg/kg riluzole either by p.o. gavage or i.v. when tumor volume had reached 6 mm$^3$. Mice were treated every day for 18 days, and tumor sizes were measured twice weekly with a Vernier caliper. A significant reduction in tumor volume was observed in mice treated with 7.5 mg/kg riluzole by either i.v. (FIG. 6A) or p.o. gavage (FIG. 6B) compared with untreated or vehicle-treated controls. Bars represent SD; *, P<0.01, compared with untreated and DMSO treated (t test).

Example 7

Phase 0 Trial of Riluzole in Patients with Resectable Stage III and IV Melanoma

Five patients diagnosed with melanomas that expressed Grm1 participated in the trial. Two weeks of therapy with riluzole at 200 mg/day (100 mg every 12 hours) resulted in little toxicity. The only toxic side effect was grade 2 dizziness in two patients. All patients were able to complete the regimen and undergo pre and post treatment biopsy and PET scanning. Four of the five patients has significant decreases in the metabolic activity of their tumors as judged by PET scanning with two patients having a 90% decrease in PET intensity. The same four patients had a statistically significant decrease in the level of activated ERK (by quantitative Western Blotting) in the post treatment specimen as compared to the pre-operative specimen demonstrating a suppression of signaling through the MAPK pathway in these patients. All 5 patients had a decrease in Ki-67 staining in the post-treatment specimen as compared to the pre-treatment specimen demonstrating a decrease in proliferation.

Example 8

Inhibition of Human Breast Cancer Cell Proliferation by GRM1 Antagonists

Grm1 mRNA and protein were detected in BT-549 breast cancer cells using quantitative real time-PCR and immunohistochemistry (data not shown). BT-549 breast cancer cells were cultured in glutamate-free medium supplemented with Glutamax and the cells serum-starved for 24 hours. After serum starvation, the breast cancer cells were incubated with L-Quisqualate (10-5M) for different time periods, after which the cells were harvested and total protein extracted for Western blotting with anti-phosphoERK antibodies.

Breast cancer cells treated with L-Quisqualate (e.g., a Grm1 agonist) alone showed more than a 130-fold increase in phospho-ERK1/2 protein levels after 5 minutes of treatment. Pre-incubation of breast cancer cells with the competitive Grm1 antagonist, LY367385, resulted in inhibition of ERK1/2 phosphorylation.

| Induction of BT-549 | | | | | | | | | |
|---|---|---|---|---|---|---|---|---|---|
| Incubation with L-Quisqualate | | | | | Pre-incubation with LY-367385 | | | | |
| Min of incubation | | | | | | | | | |
| 0 | 2 | 3 | 5 | 10 | 0 | 2 | 3 | 5 | 10 |
| Fold over baseline 1.00 | 8.89 | 51.52 | 131.06 | 120.80 | 1.00 | 1.29 | 1.01 | 1.29 | 0.80 |

Inhibition of phospho-ERK1/2 can reduce MAPK signaling and can inhibit cell proliferation.

This experiment was repeated using the Grm1 antagonists, riluzole (50 µM) and JNJ16259685 (10 µM) (both from Tocris Bioscience, Elliville, Mo.). Both compounds were able to completely inhibit L-Quisqualate-induced ERK1/2 activation (data not shown), similar to LY367385.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating breast cancer in a patient diagnosed with a breast cancer characterized by glutamate release or a breast cancer expressing glutamate receptor, metabotropic 1 (GRM1), said method comprising administering to said patient an amount of 2-amino-6-trifluoromethoxybenzothiazole (riluzole) effective to reduce breast cancer cell growth, proliferation or metastasis.

2. The method of claim 1, wherein the breast cancer expresses glutamate receptor, metabotropic 1 (GRM1).

3. The method of claim 1, further comprising administering an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, or a combination thereof.

4. The method of claim 3, wherein said chemotherapeutic agent is selected from the group consisting of 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine[1,1-cyclobutane-dicarboxylato (2-)-0,0']-,(SP-4-2) (carboplatin); and 5β,20-Epoxy-1,2α, 4,7β,10β,13α-hexahydroxytax-11-en-9-one 4,10-diacetate 2-benzoate 13-ester with (2R,3S)—N-benzoyl-3-phenylisoserine (paclitaxel).

5. The method of claim 3, wherein said B-raf inhibitor is 4-(4-{3-[4-chloro-3-(trifluoromethyl)phenyl]ureido}phenoxy)-N2-methylpyridine-2-carboxamide 4-methylbenzenesulfonate (sorafenib).

6. The method of claim 3, wherein said anti-apoptosis inhibitor is a Bcl-2 inhibitor.

7. The method of claim 3, wherein said benzoquinone ansamycin antibiotic is geldanamycin or 17-N-allylamino-17-demethoxygeldanamycin.

8. The method of claim 3, wherein said anti-angiogenisis agent is bevacizumab.

9. A method for reducing growth of a glutamate-releasing or GRM1-expressing breast cancer tumor in a subject in need thereof, comprising administering to a subject having a glutamate-releasing or GRM1-expressing breast cancer tumor an amount of 2-amino-6-trifluoromethoxybenzothiazole (riluzole) effective to reduce one or more of tumor cell growth, proliferation, and metastasis.

10. The method of claim 9, wherein the glutamate-releasing breast cancer tumor expresses GRM1.

11. The method of claim 9, further comprising administering an anti-proliferative agent, a chemotherapeutic agent, a B-raf inhibitor, a PI3K inhibitor, an anti-apoptosis inhibitor, a benzoquinone ansamycin antibiotic, an anti-angiogenesis agent, or a combination thereof.

12. The method of claim 11, wherein said chemotherapeutic agent is selected from the group consisting of 3,4-dihydro-3-methyl-4-oxoimidazo[5,1-d]-as-tetrazine-8-carboxamide (temozolomide); 5-(3,3-dimethyl-1-triazeno)-imidazole-4-carboxamide (dacarbazine); platinum, diammine[1,1-cyclobutane-dicarboxylato (2-)-0,0']-,(SP-4-2) (carboplatin); and 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine (paclitaxel).

13. The method of claim 11, wherein said B-raf inhibitor is 4-(4-{3-[4-chloro-3-(trifluoromethyl)phenyl]ureido}phenoxy)-N2-methylpyridine-2-carboxamide 4-methylbenzenesulfonate (sorafenib).

14. The method of claim 11, wherein said anti-apoptosis inhibitor is a Bcl-2 inhibitor.

15. The method of claim 11, wherein said benzoquinone ansamycin antibiotic is geldanamycin or 17-N-allylamino-17-demethoxygeldanamycin.

16. The method of claim 11, wherein said anti-angiogenesis agent is bevacizumab.

17. The method of claim 9, wherein the riluzole is administered prior to surgical excision of at least a portion of the tumor.

18. The method of claim 9, wherein the riluzole is administered following surgical excision of at least a portion of the tumor.

19. The method of claim 9, wherein the riluzole is administered in a chronic dose.

20. The method of claim 9, wherein the riluzole is administered orally, intravenously, or intraperitoneally.

21. A method of treating a glutamate-releasing GRM1-expressing breast cancer in a patient diagnosed with said cancer, comprising administering to said subject an amount of 2-amino-6-trifluoromethoxybenzothiazole (riluzole) effective to reduce the breast cancer cell growth, proliferation or metastasis.

22. A method of treating a glutamate-releasing breast cancer in a patient diagnosed with said cancer, comprising administering to said patient an amount of 2-amino-6-trifluoromethoxybenzothiazole (riluzole) effective to reduce one or more of cancer cell growth, proliferation, and metastasis.

* * * * *